United States Patent
Zhang

(10) Patent No.: US 12,017,996 B2
(45) Date of Patent: *Jun. 25, 2024

(54) SUBSTITUTED QUINOLINES AND FORMULATIONS THEREOF

(71) Applicant: JIANGSU MEDOLUTION LTD, Taizhou (CN)

(72) Inventor: Dawei Zhang, Thousand Oaks, CA (US)

(73) Assignee: Jiangsu Medolution Ltd, Taizhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/740,364

(22) Filed: May 10, 2022

(65) Prior Publication Data

US 2022/0371999 A1 Nov. 24, 2022

Related U.S. Application Data

(60) Provisional application No. 63/186,755, filed on May 10, 2021.

(51) Int. Cl.
*C07D 215/54* (2006.01)
*C07D 401/04* (2006.01)

(52) U.S. Cl.
CPC ......... *C07D 215/54* (2013.01); *C07D 401/04* (2013.01)

(58) Field of Classification Search
CPC .......... C07D 215/44; A61K 31/4706
See application file for complete search history.

(56) References Cited

U.S. PATENT DOCUMENTS

| 8,748,453 B2 * | 6/2014 | Zhang | C07D 215/56 546/152 |
| 2023/0000855 A1 * | 1/2023 | Tang | A61K 31/4709 |

FOREIGN PATENT DOCUMENTS

WO WO 2021/104340 * 6/2021

OTHER PUBLICATIONS

Simone, Oncology: Introduction, Cecil Textbook of Medicine, 20th Edition, vol. 1, pp. 1004-1010, 1996.*
Gura, Systems for identifying New Drugs are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Acute Leukemia, Merck Manual (Online Edition) 6 pages, pp. 1-6 (2013).*

* cited by examiner

*Primary Examiner* — Deepak R Rao
(74) *Attorney, Agent, or Firm* — Feng Tian

(57) ABSTRACT

The present disclosure is directed to formulations of novel quinolines and their pharmaceutically acceptable salts, which are useful for the treatment of protein kinases mediated diseases and conditions. The compounds of this disclosure have a general Formula I

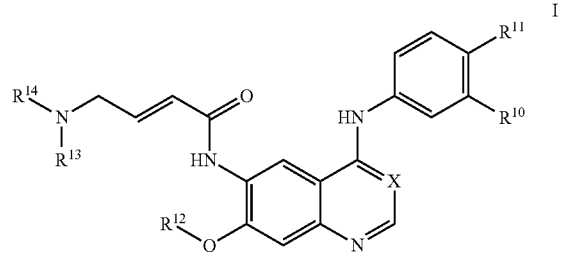

wherein $R^{10}$ to $R^{14}$ and X are defined herein.

15 Claims, 1 Drawing Sheet

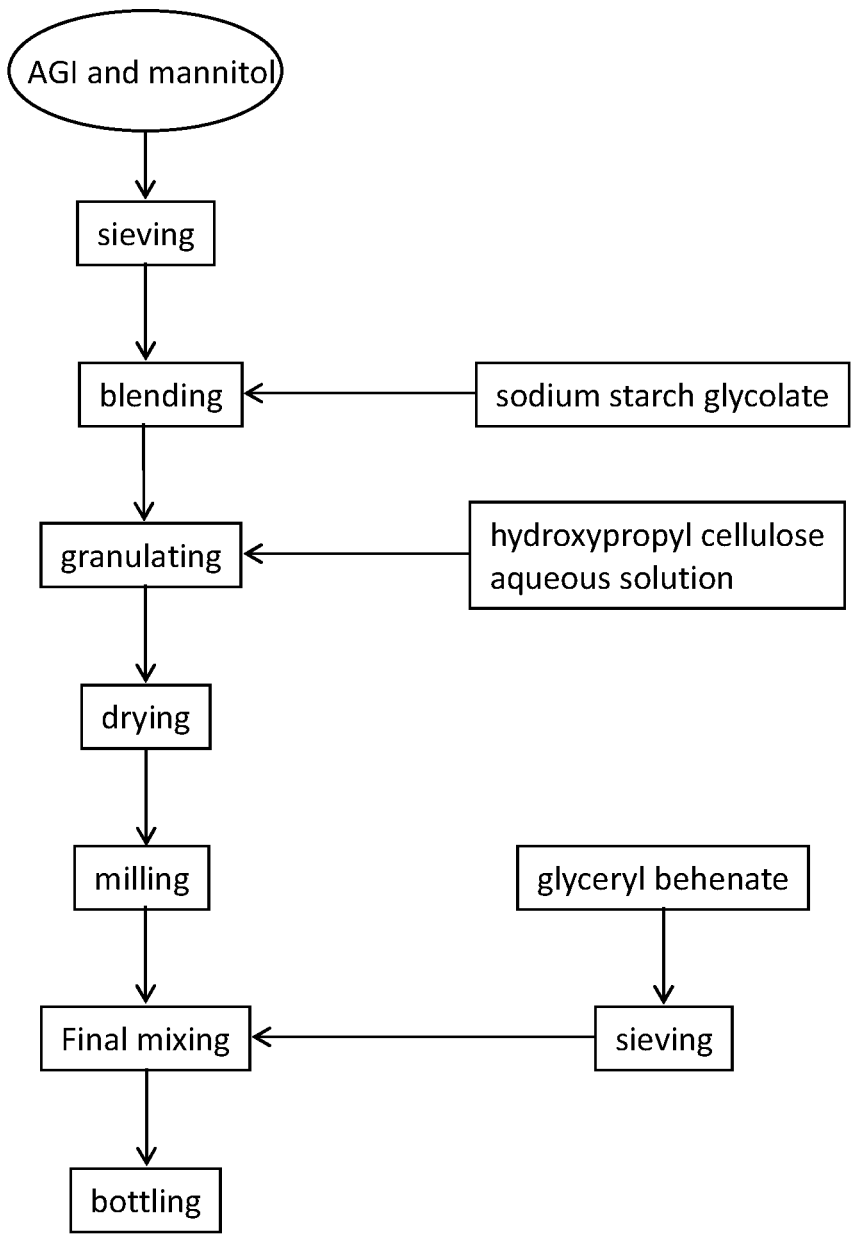

SUBSTITUTED QUINOLINES AND FORMULATIONS THEREOF

CROSS REFERENCE

This present disclosure claims the benefits of U.S. Provisional Patent Application No. 63/186,755 filed May 10, 2021, which is herein incorporated by reference in its entirety.

FIELD OF THE INVENTION

The present invention is directed to formulations of substituted quinolines, the preparation thereof, and the use of such formulations to treat kinase mediated diseases and conditions such as cancer.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. Examples of kinases in the protein kinase family include, without limitation, abl1 (v-abl Abelson murine leukemia viral oncogene homolog 1), Akt, Alk, bcr-abl1, c-kit, c-Met, c-src, c-fms, CDK1-10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Fyn, Hck, IGF-1R, Jak, KDR, Lck, Lyn, MEK, PDGFR, PIK, PKC, PYK2, ros, tie, tie2, TRK, Yes, and Zap70. Due to their activity in numerous cellular processes, kinases have emerged as important therapeutic targets.

Epidermal growth factor (EGF) is a widely distributed growth factor that in cancer, can stimulate cancer-cell proliferation, block apoptosis, activate invasion and metastasis, and stimulate angiogenesis (Citri, et al., *Nat. Rev. Mol. Cell. Biol.* 7:505, 2006; Hynes, et al., *Nat. Rev. Cancer* 5:341, 2005). The EGF receptor (EGFR or ErbB) is a transmembrane, tyrosine kinase receptor that belongs to a family of four related receptors. The majority of human epithelial cancers are marked by functional activation of growth factors and receptors of this family (Ciardiello, et al., *New Eng. J. Med.* 358: 1160, 2008) so that EGF and EGFR are natural targets for cancer therapy.

One member of the EGFR family is ErbB2 (also referred to as the neu or HER-2). The ErbB2 gene is often found amplified in breast or ovarian cancer and in glioblastoma. Over expression of ErbB2 has been demonstrated to lead to increased tumorigenicity, tumor invasiveness, increased metastatic potential, and altered sensitivity to hormonal and chemotherapeutic agents in transfection studies in cellular and animal models (Pegram, et al., *Oncogene,* 15, 537-547, 1997).

SUMMARY OF THE INVENTION

In one aspect, the present disclosure provides a pharmaceutical formulation comprising:
(i) a compound of Formula I:

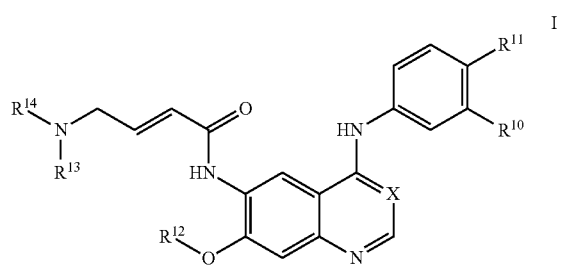

or a pharmaceutically acceptable salt thereof, wherein the amount of the compound in the pharmaceutical formulation is from 5% to 10% w/w, and wherein:
X is C—CN;
$R^{10}$ is selected from hydrogen, deuterium, $CH_3$, $CD_3$, $CH_2D$, $CHD_2$, F, Cl, $CF_3$, CN, ethynyl and ethynyl-d;
$R^{11}$ is selected from hydrogen, deuterium, $CH_3$, $CD_3$, $CH_2D$, $CHD_2$, F, Cl, $CF_3$, 3-fluorobenzyloxy, and pyridin-2-ylmethoxy;
$R^{12}$ is selected methyl, methyl-$d_3$, ethyl, ethyl-$d_3$, 2-methoxyethyl, and 2-methoxy-$d_3$-ethyl;
each of $R^{13}$ and $R^{14}$ is independently selected from hydrogen, deuterium, $CH_3$, $CD_3$, $CH_2D$, and $CHD_2$; and
provided that $R^{10}$ to $R^{14}$ contain at least one deuterium atom;
(ii) a filler;
(iii) a disintegrant;
(iv) a binder; and
(v) a lubricant.

In some embodiments, $R^{10}$ is Cl, ethynyl or ethynyl-d. In some embodiments, $R^{11}$ is 3-fluorobenzyloxy or pyridin-2-ylmethoxy. In some embodiments, each of $R^{13}$ and $R^{14}$ is independently selected from $CH_3$, and $CD_3$.

In another aspect, herein provides a pharmaceutical formulation comprising:
(i) a compound of Formula II:

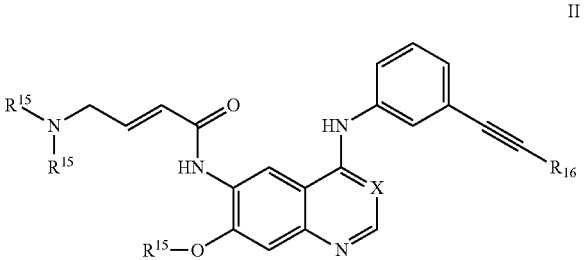

or a pharmaceutically acceptable salt thereof, wherein the amount of the compound in the pharmaceutical formulation is from 5% to 10% w/w, and wherein:
X is C—CN;
$R^{15}$ is independently $C_1$-$C_6$ alkyl or $C_1$-$C_6$ deuterated alkyl; and
$R^{16}$ is hydrogen or deuterium;

(ii) a filler;
(iii) a disintegrant;
(iv) a binder; and
(v) a lubricant.

In still another aspect, herein provides a pharmaceutical formulation comprising:
(i) Compound A:

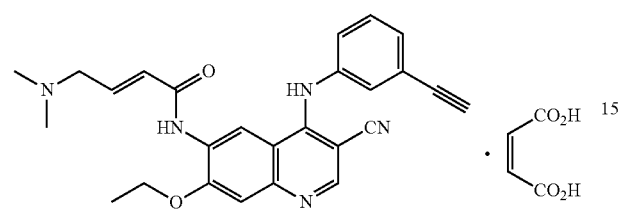

Compound A wherein the amount of the Compound A in the pharmaceutical formulation is from 5% to 10% w/w;
(ii) a filler;
(iii) a disintegrant;
(iv) a binder; and
(v) a lubricant.

In some embodiments, with respect to the pharmaceutical formulation, (i) the amount of the filler in the pharmaceutical formulation is from 80% to 90% w/w; (ii) the amount of the disintegrant in the pharmaceutical formulation is from 2% to 6% w/w; (iii) the amount of the binder in the pharmaceutical formulation is from 0.25% to 0.75% w/w; and (iv) the amount of the lubricant in the pharmaceutical formulation is from 1.5% to 4% w/w. In some embodiments, with respect to the pharmaceutical formulation, (i) the amount of the compound or Compound A in the pharmaceutical formulation is from 10 mg to 30 mg; (ii) the amount of the filler in the pharmaceutical formulation is from 160 mg to 270 mg; (iii) the amount of the disintegrant in the pharmaceutical formulation is from 4 mg to 18 mg; (iv) the amount of the binder in the pharmaceutical formulation is from 0.5 mg to 2.25 mg; and (v) the amount of the lubricant in the pharmaceutical formulation is from 3 mg to 12 mg. In some embodiments, with respect to the pharmaceutical formulation, (i) the amount of the compound or Compound A in the pharmaceutical formulation is from 15 mg to 25 mg; (ii) the amount of the filler in the pharmaceutical formulation is from 180 mg to 230 mg; (iii) the amount of the disintegrant in the pharmaceutical formulation is from 7 mg to 14 mg; (iv) the amount of the binder in the pharmaceutical formulation is from 0.8 mg to 1.45 mg; and (v) the amount of the lubricant in the pharmaceutical formulation is from 5 mg to 9 mg. In some embodiments, with respect to the pharmaceutical composition, (i) the amount of the compound or Compound A in the pharmaceutical formulation is about 20 mg; (ii) the amount of the filler in the pharmaceutical formulation is about 200 mg; (iii) the amount of the disintegrant in the pharmaceutical formulation is about 10 mg; (iv) the amount of the binder in the pharmaceutical formulation is about 1.1 mg; and (v) the amount of the lubricant in the pharmaceutical formulation is from 7 mg.

In some embodiments, the filler is mannitol. In some embodiments, the disintegrant is sodium starch glycolate. In some embodiments, the binder is hydroxypropyl cellulose. In some embodiments, the lubricant is glyceryl behenate. In some embodiments, the amount of the compound or Compound A in the pharmaceutical formulation is about 20.2 mg.

In another aspect, herein provides a pharmaceutical composition comprising: (i) about 8.4% w/w of Compound A:

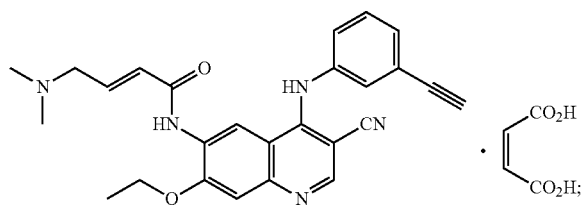

(ii) about 84% w/w mannitol; (iii) about 4.2% w/w sodium starch glycolate; (iv) about 0.46% w/w hydroxypropyl cellulose; and (v) about 2.9% w/w glyceryl behenate.

In another aspect, herein provides a pharmaceutical composition comprising: (i) about 20 mg of Compound A:

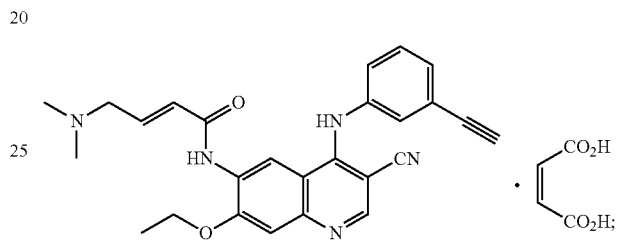

(ii) about 200 mg of mannitol; (iii) about 10 mg of sodium starch glycolate; (iv) about 1.1 mg of hydroxypropyl cellulose; and (v) about 7 mg of glyceryl behenate.

In another aspect, herein provides a pharmaceutical formulation comprising: (i) about 6.7% w/w of Compound B:

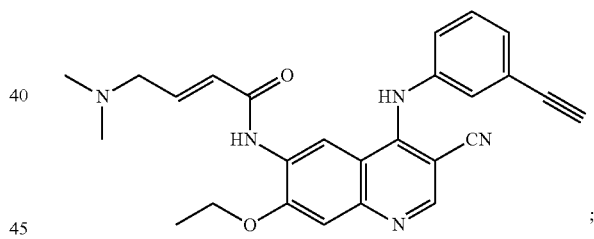

(ii) about 84% w/w mannitol; (iii) about 4.2% w/w sodium starch glycolate; (iv) about 0.46% w/w hydroxypropyl cellulose; and (v) about 2.9% w/w glyceryl behenate.

In another aspect, herein provides a pharmaceutical formulation comprising (i) about 16 mg of Compound B:

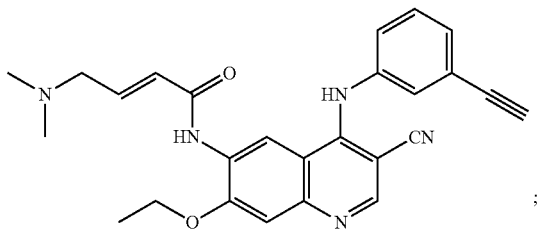 [SMILES: C#Cc1cccc(Nc2c(C#N)cnc3cc(OCC)c(NC(=O)/C=C/CN(C)C)cc23)c1]

(ii) about 200 mg of mannitol; (iii) about 10 mg of sodium starch glycolate; (iv) about 1.1 mg of hydroxypropyl cellulose; and(v) about 7 mg of glyceryl behenate.

In some embodiments, a capsule comprises the pharmaceutical formulation disclosed herein. In some embodiments, a dry-filled capsule comprising the pharmaceutical formulation disclosed here.

In another aspect, herein provides a method for preparing a pharmaceutical formulation, comprising: (a) sieving each of 5-10 weight percent of Compound A, 80-90 weight percent of one or more fillers, and 1.5-4 weight percent of one or more lubricants separately; (b) dissolving 0.25-0.75 weight percent of one or more binders into water to make a solution having a concentration of 3 weight percent with respect to the one or more binders; (c) stirring and shearing a mixture of the Compound A, the one or more fillers and 2-6% weight percent of one or more disintegrants; (d) adding the solution of the one or more binders in (b) to the mixture in (c) to make a wet mixture; (e) preparing wet pellets from the wet mixture in (d); (f) drying the wet pellets in (e) to make dried pellets; (g) sieving the dried pellets in (f) to make sifted pellets; and (h) mixing the one or more lubricants to the sifted pellets in (g); wherein Compound A is:

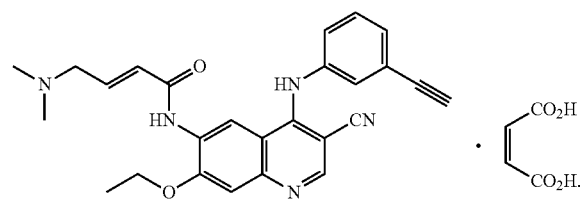 [SMILES: C#Cc1cccc(Nc2c(C#N)cnc3cc(OCC)c(NC(=O)/C=C/CN(C)C)cc23)c1 ; O=C(O)/C=C\C(=O)O]

In some embodiments, the sieving in (a) is sifted through 60 mesh sieve. In some embodiments, the wet pellets in (e) is about 20 mesh in size. In some embodiments, the sieving in (g) is sifted through 20 mesh sieve. In some embodiments, with respect to the method, (i) the one or more fillers is mannitol; (ii) the one or more disintegrants is sodium starch glycolate; (iii) the one or more binders is hydroxypropyl cellulose; and (iv) the one or more lubricants is glyceryl behenate.

In another aspect, herein provides a method for treating non-small cell lung cancer (NSCLC) in a subject, comprising: administering to the subject a therapeutically effective amount of Compound B:

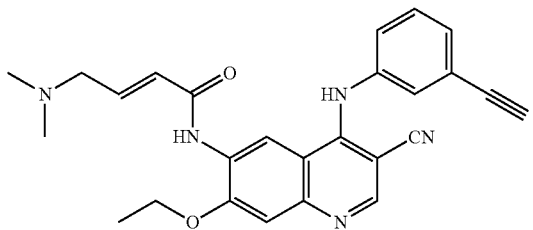

In some embodiments, the Compound B is used in monotherapy or in combination with another anti-cancer agent. In some embodiments, the other anti-cancer agent is topoisomerase inhibitors, mitosis inhibitors, compounds which interact with nucleic acids, hormone antagonists, inhibitors of metabolic processes, cytokines, an anti-neoplastic agent, an immunosuppressant, an immunostimulant, one or more antibodies, or a combination thereof.

In another aspect, herein provides a method for treating neoplasia in a subject, comprising: administering an effective amount of a pharmaceutical formulation disclosed herein.

In some embodiments, the neoplasia is selected from non-small cell lung cancer, breast cancer, leukemias, colon carcinoma, renal cell carcinoma, gastrointestinal stromal cancer, solid tumor cancer, brain cancer, glioblastoma, multiple myeloma, pancreatic carcinoma, non-hodgkin's lymphoma, hepatocellular carcinoma, thyroid cancer, bladder cancer, colorectal cancer, and prostate cancer. In some embodiments, the neoplasia is non-small cell lung cancer or breast cancer. In some embodiments, the method further comprises: administering one or more anti-cancer agents to the subject. In some embodiments, the one or more anti-cancer agents are topoisomerase inhibitors, mitosis inhibitors, compounds which interact with nucleic acids, hormone antagonists, inhibitors of metabolic processes, cytokines, an anti-neoplastic agent, an immunosuppressant, an immunostimulant, or one or more antibodies, or a combination thereof.

BRIEF DESCRIPTION OF THE DRAWINGS

FIG. 1: shows flow chart for the process of preparing the pharmaceutical formulation disclosed herein.

DETAILED DESCRIPTION OF THE INVENTION

While preferred embodiments of the present disclosure have been shown and described herein, it will be obvious to those skilled in the art that such embodiments are provided by way of example only. Numerous variations, changes, and substitutions occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

Definitions

As used herein, the term "comprising" is meant to be open-ended, including the indicated component(s), but not excluding other elements.

As used herein, the recitation of a numerical range for a variable is intended to convey that the variable is equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 1 and 3 takes the values 1, 2 or 3 if the variable is inherently discrete, and takes the values 1.0, 1.1, 1.01, 1.001, or any other real values$\geq$1 and $\leq$3 if the variable is inherently continuous.

As used herein, the term "on average" generally refers to the mean value derived from performing at least three independent replicates for each data point.

As used herein, the term "biological activity" generally refers to the structural and functional properties of a compound disclosed in the present disclosure. Biological activity is, for example, structural stability, affinity for a target, resistance to proteolytic degradation, cell penetrability, intracellular stability, in vivo stability, or any combination thereof.

As used herein, the term "pharmaceutically acceptable salt" refers to those salts which are suitable for pharmaceutical use, preferably for use in humans and lower animals without undue irritation, allergic response and the like. Pharmaceutically acceptable salts of amines, carboxylic acids, and other types of compounds. For example, S. M. Berge, et al., describe pharmaceutically acceptable salts in detail in J Pharmaceutical Sciences, 66: 1-19 (1977), incorporated herein by reference. The salts can be prepared in situ during the final isolation and purification of the substituted quinolines of this disclosure, or separately by reacting a free base or free acid function with a suitable reagent, as described generally below. For example, a free base function can be reacted with a suitable acid. Suitable pharmaceutically acceptable salts can include metal salts, such as alkali metal salts, e. g. sodium, potassium, and lithium salts; and alkaline earth metal salts, e. g. calcium or magnesium salts. Examples of pharmaceutically acceptable, nontoxic acid addition salts are salts of an amino group formed with inorganic acids such as hydrochloric acid, hydrobromic acid, hydroiodic acid, phosphoric acid, sulfuric acid and perchloric acid; or with organic acids such as acetic acid, oxalic acid, maleic acid, tartaric acid, citric acid, succinic acid, or malonic acid; or by using other methods used in the art such as ion exchange. Other pharmaceutically acceptable salts include adipate, alginate, ascorbate, aspartate, benzoate, bisulfate, borate, butyrate, camphorate, camphorsulfonate, citrate, cyclopentanepropionate, digluconate, dodecylsulfate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, nicotinate, nitrate, oleate, oxalate, palmitate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Additional examples of such salts can be found in Berge et al., J. Pharm. Sci., 66, 1 (1977). Conventional methods, in some embodiments, are used to form the salts. For example, a phosphate salt of a compound of the disclosure is made by combining the desired compound free base in a desired solvent, or combination of solvents, with phosphoric acid in a desired stoichiometric amount, at a desired temperature, typically under heat (depending upon the boiling point of the solvent). In one embodiment, the salt is precipitated upon cooling (slow or fast) and crystallize (i.e., if crystalline in nature). Further, hemi-, mono-, di, tri- and poly-salt forms of the compounds of the present disclosure are also contemplated herein. Similarly, hemi-, mono-, di-, tri- and poly-hydrated forms of the compounds, salts and derivatives thereof, are also contemplated herein.

As used herein, the term "w/w" generally refers to weight per weight, or weight concentration for a component of a formulation. For example, if 5 g sugar is dissolved in 20 g of water. The concentration of sugar in this solution is 20% w/w.

As used herein, the term "pharmaceutical composition" generally refers to a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "stability" generally refers to chemical stability and/or physical stability. As used herein, the phrase "chemical stability" generally refers to the ability of a compound to maintain its chemical identity over time. Accordingly, stability implies the ability of a chemical species to resist oxidation or other degradation, for example. As used herein, the phrase "physical stability" refers to the ability of a composition to maintain consistent physical properties over time. The ability of a composition to maintain a consistent disintegration time over time is exemplary of physical stability.

As used herein, the term "alkyl" generally refers to straight chain and branched aliphatic hydrocarbon groups, generally having a specified number of carbon atoms (i.e., $C_1$-$C_8$ alkyl refers to an alkyl group having from 1 to 8 carbon atoms, inclusive). Examples of alkyl groups include, without limitation, methyl, ethyl, n-propyl, i-propyl, n-butyl, s-butyl, t-butyl, n-pentyl, s-pentyl, n-hexyl, and the like.

As used herein, the term "alkenyl" generally refers to linear or branched radicals having at least one carbon-carbon double bond in a moiety having between two and ten carbon atoms. Examples of alkenyl radicals include, without limitation, ethenyl, allyl, propenyl, butenyl and N,N-dimethylpropenyl. The terms "alkenyl" and "lower alkenyl", embrace radicals having "cis" and "trans" orientations, or alternatively, "E" and "Z" orientations, as appreciated by those of ordinary skill in the art.

As used herein, the term "alkynyl" generally refers to linear, cyclic or branched radicals having at least one carbon-carbon triple bond and having two to ten carbon atoms. Examples of such radicals include, without limitation, ethynyl, propynyl (propargyl), butynyl, and the like.

As used herein, the term "alkoxy" or "alkoxyl" generally refers to linear or branched oxygen-containing radicals each having alkyl portions of one or more carbon atoms. Examples of such radicals include methoxy, ethoxy, propoxy, butoxy and tert-butoxy, 2-methoxyethoxy, optionally substituted benzyloxy or optionally substituted pyridinylmethoxy, and the like.

As used herein, the term "optionally substituted alkoxy" generally refers to the carbon atom of alkyl portion of the alkoxy group is optionally substituted by H, D, F, Cl, $CF_3$ or $C_1$-$C_6$ alkoxy, $C_1$-$C_6$ alkylamino. The alkyl portion usually having from 1 to 8 carbon atoms.

As used herein, the term "halo" or "halogen" or "halide" generally refers to halogens such as fluorine, chlorine, bromine or iodine atoms.

As used herein, the term "aminocarbonyl" generally refers to nitrogen-containing radicals attached to a carbonyl group substituted by $C_1$-$C_8$ alkyl or $C_2$-$C_8$ alkenyl groups. The each carbon atom of alkyl portion inside the $C_1$-$C_8$ alkyl or $C_2$-$C_8$ alkenyl groups is optionally substituted by H, D, F, Cl, $CF_3$ or $C_1$-$C_6$ alkoxy, $C_1$-$C_6$ alkylamino.

As used herein, the term "aminoalkyl" and "alkylamino" generally refers to $H_2N$-alkyl, alkyl-NH—, alkyl-NH-alkyl, (alkyl)$_2$N-alkyl, wherein alkyl is defined above.

As used herein, the term "derivative" generally refers to any salt of a compound of this disclosure, any ester of a compound of this disclosure, or any other compounds, which upon administration to a patient is capable of providing (directly or indirectly) a compound of this disclosure, or a metabolite or residue thereof, characterized by the ability to modulate a kinase enzyme.

As used herein, the term, the terms "increase" and "decrease" generally refers, respectively, to cause a statistically significantly (i.e., $p<0.1$) increase or decrease of at least 5%.

As used herein, the term "prodrug" generally refers to a compound which upon administration to a subject or patient is capable of providing (directly or indirectly) a compound of this disclosure. A "pharmaceutically-acceptable prodrug" as used herein, denotes a prodrug, which is pharmaceutically acceptable.

In some embodiments, the compound(s) of this disclosure are used to treat a subject by administering the compound(s) as a pharmaceutical composition. To this end, the compound(s), in one embodiment, are combined with one or more pharmaceutically acceptable excipients, including carriers, diluents or adjuvants, to form a suitable composition, which is described in more detail herein.

As used herein, the term "excipient" generally refers to any pharmaceutically acceptable additive, carrier, adjuvant, or other suitable ingredient, other than the active pharmaceutical ingredient (API), which is typically included for formulation and/or administration purposes.

As used herein, the term "filler" or "diluent" generally refers to an agent used to achieve the desired composition volume or weight. The filler or diluent may be present in the pharmaceutical composition within granules in the form of a single compound or in the form of a mixture of compounds. Non-limiting examples of diluent include lactose, starch, pregelatinized starch, microcrystalline cellulose, silicified microcrystalline cellulose, cellulose acetate, dextrose, mannitol, sodium phosphate, potassium phosphate, calcium phosphate, fructose, maltose, sorbitol, or sucrose.

As used herein, the term "adjuvant" generally refers to any substance or mixture of substances that increases the efficacy or potency of a compound disclosed herein on a target where the adjuvant is used together with the compound disclosed herein. However, when the adjuvant is used alone, no pharmacological effect is observed on the same target.

As used herein, the terms "treat", "treating," "treatment," and "therapy" generally refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

As used herein, the term "therapeutically effective amount" or "effective amount" generally refers to quantifying the amount of each agent, which can achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Regardless of the route of administration selected, the compounds of the present disclosure, which may be used in a suitable hydrated form, and/or the pharmaceutical compositions of the present disclosure, are formulated into pharmaceutically acceptable dosage forms or by other conventional methods known to those of skill in the art.

Actual dosage levels of the active ingredients in the pharmaceutical compositions of the present disclosure may be varied so as to obtain an effective amount of the active ingredient to achieve the desired therapeutic response for a particular patient, composition, and mode of administration, without being toxic to the patient.

The selected dosage level can depend upon a variety of factors including the activity of the particular compound of the present disclosure employed, the route of administration, the time of administration, the rate of excretion of the particular compound being employed, the duration of the treatment, other drugs, compounds and/or materials used in combination with the particular hedgehog inhibitor employed, the age, sex, weight, condition, general health and prior medical history of the patient being treated, and like factors.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure can be that amount of the compound which is the lowest dose effective to produce a therapeutic effect. Such an effective dose can generally depend upon the factors described above. Generally, doses of the compounds of this disclosure for a patient can range from about 0.0001 to about 100 mg per kilogram of body weight per day. The mode of administration can have a large effect on dosage. Higher doses may be used for localized routes of delivery.

If desired, the effective daily dose of the active compound may be administered as two, three, four, five, six or more sub-doses administered separately at appropriate intervals throughout the day, optionally, in unit dosage forms. Those of skill in the art can readily appreciate that dose levels can vary as a function of the specific compound, the severity of the symptoms and the susceptibility of the subject to side effects. Dosages for a given compound disclosed herein are readily determinable by those of skill in the art by a variety of means.

As used herein, the term "unit dosage form" generally refers to a physically discrete unit of the disclosed formulation appropriate for the subject to be treated. The total daily usage of the compositions of the present disclosure will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors.

As used herein, the term "therapeutically active agent" or "active agent" generally refers to a substance, including a biologically active substance, that is useful for therapy (e.g., human therapy, veterinary therapy), including prophylactic and therapeutic treatment. Therapeutically active agents may include organic molecules that are drug compounds, peptides, proteins, carbohydrates, monosaccharides, oligosaccharides, polysaccharides, nucleoprotein, mucoprotein, lipoprotein, synthetic polypeptide or protein, small molecules linked to a protein, glycoprotein, steroid, nucleic acid, DNA, RNA, nucleotide, nucleoside, oligonucleotides, antisense oligonucleotides, lipid, hormone, and vitamin. Therapeutically active agents may include any substance used as a medicine for treatment, prevention, delay, reduction or amelioration of a disease, condition, or disorder. A therapeutically active agent includes a compound that increases the effect or effectiveness of a second compound, for example, by enhancing potency or reducing adverse effects of a second compound.

Indication

The present disclosure provides compounds which are capable of modulating one or more signal transduction pathways comprising, but not limited to, EGFR and/or ErbB2. EGFR and/or ErbB2 are an important signaling molecule involved in the regulation of a number of key cellular processes, including cell growth, cell survival and invasion.

The compounds of the present disclosure can also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation) etc.

By the term "modulate," it is meant that the functional activity of the pathway (or a component of it) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

In some embodiments, the compounds of the present disclosure can be used to treat and/or prevent any disease or condition involving one or more cellular signal transduction pathways comprising EGFR and/or ErbB2.

Any tumor or cancer can be treated, including, but not limited to, cancers having one or more mutations in EGFR and/or ErbB2, as well as any upstream or downstream member of the signaling pathways of which they are a part. As discussed earlier, a cancer can be treated with a compound of the present disclosure irrespective of the mechanism which is responsible for it.

The disclosure also provides methods for treating, preventing, modulating, etc., diseases and conditions in mammals comprising administering a compound of this disclosure with another modulator of the signal transduction pathway comprising, but not limited to EGFR and/or ErbB2. These can be present in the same composition or in separate formulations or dosage units. Administration can be the same or different routes, and can be simultaneous, sequential, etc. These methods generally involve administering effective amounts of compounds of the present disclosure, where an effective amount is the quantity of the compound which is useful to achieve the desired result. Compounds can be administered in any effective form by any effective route, as discussed in more detail below.

Methods include modulating tumor cell proliferation, including inhibiting cell proliferation. The latter indicates that the growth and/or differentiation of tumor cells is reduced, decreased, diminished, slowed, etc. The term "proliferation" includes any process which relates to cell growth and division, and includes differentiation and apoptosis. Any amount of inhibition is considered therapeutic.

Any tumor or cancer can be treated, including, but not limited to, cancers having one or more mutations in EGFR and/or ErbB2, as well as any upstream or downstream member of the signaling pathways of which they are a part. As discussed earlier, a cancer can be treated with a compound of the present disclosure irrespective of the mechanism which is responsible for it. Cancers of any organ can be treated, including cancers of, but not limited to, e.g., colon, pancreas, breast, prostate, bone, liver, kidney, lung, testes, skin, pancreas, stomach, colorectal cancer, renal cell carcinoma, hepatocellular carcinoma, melanoma, etc.

Examples of breast cancer include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumor.

Tumors of the male reproductive organs include, but are not limited to, prostate and testicular cancer. Tumors of the female reproductive organs include, but are not limited to, endometrial, cervical, ovarian, vaginal, and vulvar cancer, as well as sarcoma of the uterus.

Tumors of the digestive tract include, but are not limited to, anal, colon, colorectal, esophageal, gallbladder, gastric, pancreatic, rectal, small-intestine, and salivary gland cancers.

Tumors of the urinary tract include; but are not limited to, bladder, penile, kidney, renal pelvis, ureter, and urethral cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, and/or oropharyngeal cancers, and lip and oral cavity cancer.

Lymphomas include, but are not limited to, AIDS-related lymphoma, non-Hodgkin's lymphoma, cutaneous T-cell lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

In addition to inhibiting the proliferation of tumor cells, compounds of the present disclosure can also cause tumor regression, e.g., a decrease in the size of a tumor or in the extent of cancer in the body.

The present disclosure relates to a method for using the compounds or the formulations disclosed herein to treat mammalian hyper-proliferative disorders and/or angiogenesis disorders (e.g. cancers). This method comprises administering to a mammal in need thereof, including a human, an amount of a formulation of this disclosure, which is effective to treat the disorder. Hyper-proliferative disorders include but are not limited to cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemia.

The amount of compound(s) which is/are administered and the dosage regimen for treating cancer with the compounds and/or formulations of this disclosure depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. In some embodiments, a daily dose of about 0.01 to 500 mg/kg, 0.01 to 100 mg/kg, advantageously about 0.01-50 mg/kg, more advantageously about 0.05-30 mg/kg, even more advantageously about 0.1-10 mg/kg, and even more advantageously about 0.1-5 mg/kg body weight are appropriate, and should be useful for all methods of use disclosed herein. The daily dose can be administered in one to four doses per day.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

Some Aspects of the Problem to be Solved

As used herein, the term "previous formulation" or "previous pharmaceutical composition" generally refers to a formulation or pharmaceutical composition comprising: Compound A ((E)-N-[3-cyano-7-ethoxy-4-(3-ethynylanilino)-6-quinolyl]-4-(dimethylamino)but-2-enamide maleate, about 20 mg), microcrystalline cellulose 102 (about 170 mg), and colloidal silicon dioxide (about 0.96 mg) in a gelatin hollow capsule.

Compound A is a maleate salt of a substituted quinoline and exhibits low solubility in water and alcohol. For example, Compound A is soluble in acetic acid and hydrochloric acid solution (0.1 M). It is slightly soluble in acetonitrile and ethanol, and extremely slightly soluble in water. It is hardly soluble in n-propanol, and not soluble in sodium hydroxide solution (0.1 M). Compound A's dissociation constants: pKa1 is 4.99; pKa2 is 10.26. The previous pharmaceutical composition exhibits poor stabilities under the accelerated conditions (temperature 40±2° C./relative humidity (RH) 75±5%). In particular, the amount of impurity SZMD4-Z8 increased significantly under the accelerated conditions.

Compound B is ((E)-N-[3-cyano-7-ethoxy-4-(3-ethynylanilino)-6-quinolyl]-4-(dimethylamino)but-2-enamide. Compound A is a maleate salt of Compound B.

SZMD4-Z8:

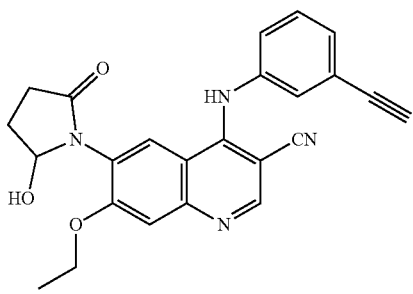 [SMILES: C#Cc1cccc(Nc2c(C#N)cnc3cc(OCC)c(N4C(=O)CCC4O)cc23)c1]

Compound A exhibits less favorable flowability and low aqueous solubility, either of which can contribute to problems such as tableting or uniformity of dosage units. The previous process to prepare the previous pharmaceutical composition comprises mixing the ingredients (including the active ingredient and excipients) to afford an intermediate mixed ingredients, then filling the capsule with the intermediate mixed ingredients. Compound A can also be a sticky and cohesive material during the formulation process, including, for example, sticking to processing machines or measuring devices when filing capsules.

Compound A can exhibit less favorable flowability and low aqueous solubility, either of which can contribute to problems such as tableting or uniformity of dosage units. Compound A can also be a sticky and highly cohesive material. Compound A can be prone to degradation in moist conditions and under exposure to light. Because Compound A can be sticky and can adhere to surfaces such as tablet punch faces and dies, it can cause problems in tableting, especially on a high speed tablet press. In addition, the stability of Compound A in previously formulations may have some problems. Compound A in previous formulations can degrade over time and may have shelve life issues when stored about or longer than 12 months under normal and/or extreme testing conditions. Accordingly, novel and better formulations for Compound A are desirable to improve the properties of the formulations over previous formulations. For example, the previous pharmaceutical composition exhibits stability problems when stored more than 12 months under normal stability conditions or three month under accelerated stability conditions according to the detected amount of degradation product SZMD4-Z8.

Pharmaceutical Compositions/Formulations

One embodiment provides a pharmaceutical composition comprising Compound A or a compound of Formulas I-II, or salt and/or solvate thereof, and at least one pharmaceutically acceptable excipient.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

An active pharmaceutical ingredient (API) may display a desired pharmacological activity. In addition, a variety of chemical, physical or physicochemical characteristics of the active substance may be relevant for the preparation of solid oral dosage forms, such as, for example, oral powders, granules, pellets, tablets, capsules, chewable tablets, dispersible tablets, and lozenges. In order to achieve some adequate formulation characteristics, such as, for example, correct assay, content and mass uniformity, the drug product may need to display some desired chemical and physical stability and a proper dissolution rate. In addition, the characteristics of the product intermediates may have to be adequate for robust, fast and cost efficient processing.

Without being restrictive, examples of relevant processing parameters for the active agent (the drug substance) may include the chemical and physical stabilities of the drug substance under various environmental conditions which may strongly influence the chemical and physical stabilities of the final pharmaceutical formulation (the drug product), and other physical characteristics of the drug substance, such as, for example, bulk densities (i.e. poured and tapped density), particle morphology, shape, the ratio of length to width for needles, size distribution, electrostatic charging and surface adhesive properties, which may vary due to precipitation and drying conditions of the drug substance. These characteristics may significantly influence key features for processing of the drug substance into a final formulation, such as flowability, stickiness and compressibility.

Hydrolytic degradation may be another factor to consider if the drug substance is sensitive to moisture. If so, it may be substantial to minimize the access to moisture within the manufacture process of the drug product up to packaging. It may also require taking effective measures to prevent entrance of water into the final packaging in order to achieve an adequate shelf life of the moisture sensitive product.

For example, a moisture sensitive compound can quickly hydrolytically degrade at humid conditions, e.g. in the presence of water, moisture or moisture released by further excipients in the drug product, resulting a main API degradation product of the original API, for example, releasing dimethylamine from the side chain attached to position 6 of the quinazoline shown in Compound A. This and other degradation products can be formed over time.

Suitable pharmaceutical preparations for the use in accordance with the present disclosure may include but are not limited to, tablets, capsules, suppositories, solutions, and particularly solutions for injection (s.c., i.v., i.m.) and infusion, syrups, emulsions or dispersible powders. The amount of the pharmaceutically active compound disclosed herein in each case can vary, for example, in the range from 0.1-90 wt. %, preferably 0.5-50 wt. % of the total composition, i.e. in amounts which are sufficient to achieve the dosage range given below. The doses specified may, if necessary, be given several times a day, or once daily, once every other day, once weekly, once biweekly, etc.

Suitable tablets may be obtained, for example, by mixing the active substance(s) with known excipients. Excipients may include, for example, inert diluents such as calcium carbonate, calcium phosphate or lactose; disintegrants such as corn starch or alginic acid; binders such as starch, hydroxypropyl cellulose, or gelatin; lubricants such as magnesium stearate or talc and/or agents for delaying release, such as carboxymethyl cellulose, cellulose acetate phthalate, or polyvinyl acetate. The tablets may also comprise several layers.

Coated tablets may be prepared by coating cores produced analogously to the tablets with substances normally used for tablet coatings, for example, collidone or shellac, gum arabic, talc, titanium dioxide or sugar. To achieve delayed release or prevent incompatibilities the core of the coated tablets may consist of a number of layers. Similarly the tablet coating may consist of a number of layers to achieve delayed release, possibly using the excipients mentioned above for the tablets among other choices.

Syrups or elixirs containing the active substances or combinations thereof according to the present disclosure may additionally contain a sweetener, such as, for example, saccharin, cyclamate, glycerol or sugar and a flavor enhancer, such as, for example, a flavoring such as vanillin or orange extract. They may also contain suspension adjuvants or thickeners, such as, for example, sodium carboxymethyl cellulose, wetting agents, such as, for example, condensation products of fatty alcohols with ethylene oxide, or preservatives such as p-hydroxybenzoates.

Solutions for injection and infusion may be prepared in various ways, such as, for example, with the addition of preservatives, such as, for example, p-hydroxybenzoates; or stabilizers, such as, for example, alkali metal salts of ethylenediamine tetraacetic acid; optionally using emulsifiers and/or dispersants, while if water is used as the diluent, organic solvents may optionally be used, such as, for example, solubilizers or auxiliary solvents. Once mixed the solution may be transferred into injection vials or ampoules or infusion bottles.

Capsules containing one or more active substances or combinations of active substances in the present disclosure may, for example, be prepared by mixing the active substances with inert carriers such as lactose or sorbitol. The mixture can then be packed into gelatin capsules.

Suitable suppositories may be made, for example, by mixing with carriers provided for this purpose, such as, for example, neutral fats or polyethyleneglycol, or the derivatives thereof.

Suitable excipients may be, for example, water; pharmaceutically acceptable organic solvents, such as, for example, paraffins (e.g. petroleum fractions), oils of vegetable origin (e.g. groundnut or sesame oil), mono- or polyfunctional alcohols (e.g., ethanol or glycerol); carriers, such as, for example, natural mineral powders (e.g. kaolin, clays, talc, chalk), synthetic mineral powders (e.g., highly dispersed silica and silicates), sugar (e.g., glucose, lactose and dextrose), emulsifiers (e.g., lignin, spent sulphite liquors, methylcellulose, starch and polyvinylpyrrolidone) and lubricants (e.g., magnesium stearate, talc, stearic acid, and sodium lauryl sulphate).

The preparations can be administered in several ways, preferably by the oral or transdermal route, particularly preferably by oral route. When administered orally the tablets may contain additives, such as, for example, sodium citrate, calcium carbonate and dicalcium phosphate; together with various additives, such as, for example, starch, preferably potato starch, gelatin and the like; in addition to the abovementioned carriers. Lubricants such as magnesium stearate, sodium laurylsulphate and talc may also be used to form tablets. In the case of aqueous suspensions the active substances of the present disclosure may be combined with various flavor enhancers or colorings in addition to the abovementioned excipients. For parenteral use, solutions of the active substances of the present disclosure may be prepared using suitable liquid carrier materials.

Provided herein are pharmaceutical compositions that include a compound of Formulas I-II, or a pharmaceutically acceptable salt and/or solvate thereof, and at least one pharmaceutically acceptable inactive ingredient. In some embodiments, the compounds described herein are administered as pharmaceutical compositions in which the compound of Formulas I-II, or the pharmaceutically acceptable salt and/or solvate of thereof, is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formulas I-II, or pharmaceutically acceptable salt and/or solvate thereof, with other chemical components (i.e. pharmaceutically acceptable inactive ingredients), such as carriers, excipients, binders, filling agents, suspending agents, flavoring agents, sweetening agents, disintegrant, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

The pharmaceutical compositions described herein, which include a compound of Formulas I-II, or pharmaceutically acceptable salt and/or solvate thereof, are formulated into any suitable dosage form, including but not limited to, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients may include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrant or disintegrating agents can be added, such as the cross-linked croscarmellose sodium, polyvinylpyrrolidone, sodium starch glycolate, agar, or alginic acid or a salt thereof, such as, sodium alginate. In some embodiments, dyestuffs or pigments can be added to the tablets or dragee coatings for identification or to characterize different combinations of active compound doses. In some embodiments, excipients may include binders, such as, for example, cellulose and/or its derivatives as microcrystalline cellulose, ethylcellulose, carboxymethylcellulose, hydroxypropylmethylcellulose, hydroxyethylcellulose, hydroxypropyl cellulose, starch or modified starches (e.g. pre-gelatinized, or partially hydrolysed), polyethyleneglycols, polyvinylpyrrolidones (e.g. Kollidon® K30), polyvinylacetates, polyvinylalcohols or co-polymerisates thereof (e.g. Copovidone).

All formulations for oral administration can be in dosages suitable for such administration. Examples of such dosage units are tablets or capsules. In some embodiments, these can contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

In dry granulation (slugging or roller compaction) intragranular materials may be blended to prepare slugs or roller compaction. Material may be milled and blended with extragranular materials followed by capsule filling or tablet compression. Wet granulation may entail blending intragranular materials. Wet granulation may granulate the blend with water, with or without a binder, may use high sheer, low sheer granulators, and may dry the granules using temperatures up to 100° C. Material may be milled and blended with extragranular materials followed by capsule filling or tablet compression. See, 25 Handbook of Pharmaceutical Granulation Technology, 1997, Dilip Parikh, Marcel Dekker, Inc. ISBN 0-8247-9882-1, pages 338-368.

In some embodiments, the solid dosage forms disclosed herein can be in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation or the present disclosure can be in the form of a powder. In still other embodiments, the pharmaceutical formulation of the present disclosure can be in the form of a tablet. In other embodiments, pharmaceutical formulations of the present disclosurecan in the form of a capsule.

In some embodiments, the pharmaceutical solid oral dosage forms can be formulated to provide a controlled release of the active ingredient. Controlled release refers to the release of the active ingredient, such as, for example, Compound A, or the non-salt and/or non-hydrate forms of Compound A, from a dosage form in which it is incorporated according to a desired profile over an extended period of time. Such longer periods of response may provide for many inherent benefits that are not achieved with the corresponding short acting, immediate release preparations.

In some embodiments, the daily parenteral dosage regimen can be from about 0.05 to about 30 mg/kg, preferably from about 0.1 to about 10 mg/kg, and more preferably from about 0.1 mg to 5 mg/kg of total body weight.

Combinations

In certain embodiments, the compositions and formulations of the present disclosure, may be administered as the sole active pharmaceutical agent to treat one or more disorders as described herein, or alternatively may be administered in combination with (whether simultaneously or sequentially) one or more other active agents useful to treat one or more disorders as described herein. Thus, a disclosed composition, or formulation thereof, can be administered concurrently with, prior to, or subsequent to, one or more active agents.

In certain embodiments, the pharmaceutical compositions may include one or more other active agents, in addition to Compound A, or a compound of Formula I-II, or a pharmaceutically acceptable salt and/or solvate thereof. In some embodiments, disclosed formulations comprise both another anticancer compound and Compound A, or a compound of Formula I-II, or a pharmaceutically acceptable salt and/or solvate thereof.

The amount of additional active agent(s) present in combination compositions of this invention will typically be no more than the amount that would normally be administered in a composition comprising that active agent as the only therapeutic agent. In certain embodiments of the present invention, the amount of additional active agent will range from about 50% to 100% of the amount normally present in a composition comprising that compound as the only therapeutic agent In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formulas I-II, or a pharmaceutical acceptable salt and/or solvate thereof, is co-administered with a second therapeutic agent, wherein the compound of Formulas I-II or the pharmaceutical acceptable salt and/or solvate thereof and the second therapeutic agent modulate different aspects of the disease, disorder or condition being treated, thereby providing a greater overall benefit than administration of either therapeutic agent alone. In some embodiments, the second therapeutic agent is anti-cancer agent.

In certain embodiments, different therapeutically-effective dosages of the compounds disclosed herein can be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formulas I-II, or a pharmaceutical acceptable salt and/or solvate thereof, is initiated prior to, during, or after treatment with a second agent described herein, and continues until any time during treatment with the second agent or after termination of treatment with the second agent. It also includes treatments in which a compound of Formulas I-II, or a pharmaceutical acceptable salt and/or solvate thereof, and the second agent being used in combination are administered simultaneously or at different times and/or at decreasing or increasing intervals during the treatment period. Combination treatment further includes periodic treatments that start and stop at various times to assist with the clinical management of the patient.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills). In one embodiment, one of the therapeutic agents is given in multiple doses, and in another, two (or more if present) are given as multiple doses. In some embodiments of non-simultaneous administration, the timing between the multiple doses varies from more than zero weeks to less than four weeks. In addition, the combination methods, compositions and formulations are not to be limited to the use of only two agents; the use of multiple therapeutic combinations is also envisioned.

In one aspect, the compound of Formulas I-II, or a pharmaceutical acceptable salt and/or solvate thereof, is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and may be useful for treating cancer in combination with the compounds described herein.

Other anti-cancer agents for use in combination with the compounds of Formulas I-II, or a pharmaceutical acceptable salt and/or solvate thereof, include one or more of the following: abiraterone, adriamycin, dactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Yet other anticancer agents for use in combination with the compounds of Formulas I-II, or a pharmaceutical acceptable salt and/or solvate thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with the compounds of Formulas I-II, or a pharmaceutical acceptable salt and/or solvate thereof, include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with the compounds of Formulas I-II, or a pharmaceutical acceptable salt and/or solvate thereof, include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.).

These detailed descriptions are presented for illustrative purposes only and are not intended as a restriction on the scope of the disclosure.

New Pharmaceutically Acceptable Compositions and Formulations

In certain embodiments, the present invention provides a pharmaceutically acceptable composition and formulation comprising: Compound A. Compound A and other 4-amino-3-cyanoquinoline compounds are disclosed in U.S. Pat. No. 8,748,453. Compound A, like many 4-amino-3-cyanoquinoline compounds, can be prepared and isolated as a free base or prepared as a pharmaceutically acceptable salt, such as a maleate salt. Compound A can be a weak base with an intrinsic low solubility in water.

Compound A ((E)-N-[3-cyano-7-ethoxy-4-(3-ethynylanilino)-6-quinolyl]-4-(dimethylamino)but-2-enamide maleate):

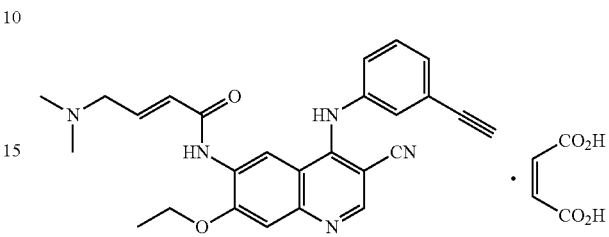

In some embodiments, the active ingredient comprises a 4-amino-3-cyanoquinoline compound or a salt and/or solvate thereof, such as Compound A, specifically Compound A. Suitable examples of 4-amino-3-cyanoquinoline compounds are disclosed in U.S. Pat. No. 8,748,453, which is incorporated herein by reference in all aspects. According to one embodiment, Compound A is the active ingredient. The active ingredient comprises from about 2 weight % to about 20 weight %, including from 5-15 weight % and about 7-10 weight % or 8.4 weight %, based upon total weight of the formulation.

In some embodiments, a filler can be used as in the formulation. Suitable fillers (also referred to as "diluents") may include but are not limited to starch, dextrin, sucrose, Sorbitol, Sodium Saccharin, Acesulfame potassium, Xylitol, Aspartame, Mannitol, starch, PVP (polyvinyl pyrrolidone), low molecular weight HPC (hydroxypropyl cellulose), microcrystalline cellulose (MCC), low molecular weight HPMC (hydroxypropyl methylcellulose), low molecular weight carboxymethyl cellulose, ethylcellulose, dicalcium phosphate, silicified microcrystalline cellulose, alginates, gelatin, polyethylene oxide, acacia, dextrin, sucrose, magnesium aluminum silicate, and polymethacrylates. Fillers include agents selected from the group consisting of microcrystalline cellulose, starch, lactitol, lactose, a suitable inorganic calcium salt, sucrose, glucose, mannitol, silicic acid, or a combination thereof. The fillers comprise from about 15 weight % to about 99 weight %, about 80-90 weight %, about 82-86 weight %, or about 84 weight % based upon total weight of the formulation. In one embodiment, the filler is mannitol.

In some embodiments, a disintegrant can be used as in the formulation. Suitable disintegrants include but are not limited to, agar, calcium carbonate, potato or tapioca starch, alginic acid, certain silicates, sodium carbonate, crospovidone (cross-linked PVP), sodium carboxymethyl starch (sodium starch glycolate), cross-linked sodium carboxymethyl cellulose (croscarmellose), pregelatinized starch (starch 1500), microcrystalline starch, water insoluble starch, sodium starch glycolate, potassium polacrilin, sodium alginate, calcium carboxymethyl cellulose, magnesium aluminum silicate (Veegum) or a combination thereof. In some embodiments, a disintegrant is sodium starch glycolate. The disintegrant comprises from about 0.5 weight % to about 10 weight %, about 2-6 weight %, or about 3-5 weight %, or about 4.2 weight %, based upon total weight of the formulation.

In some embodiments, a binder can be used as in the formulation. Suitable binders include for example, cellulose and/or its derivatives as microcrystalline cellulose, ethylcellulose, carboxymethylcellulose, hydroxypropylmethylcellulose, hydroxyethylcellulose, hydroxypropyl cellulose, starch or modified starches (e.g. pre-gelatinized, or partially hydrolysed), polyethyleneglycols, polyvinylpyrrolidones (e.g. Kollidon® K30), polyvinylacetates, polyvinylalcohols or co-polymerisates thereof (e.g. Copovidone). In some embodiments, the binder is hydroxypropyl cellulose. The amount of binders used is about 0.05-2 weight %, about 0.1-1 weight %, about 0.25-0.75 weight %, 0.4-0.5 weight %, or about 0.46 weight %, based on the total weight of the formulation.

In some embodiments, a lubricant can be used as in the formulation. Suitable lubricants or glidants include for example stearates, sodium stearyl fumarate, glyceryl behenate, magnesium salts and magnesium stearate. In some embodiments, the lubricant is glyceryl behenate. The amount of lubricants used is about 0.2-8 weight %, about 1-6 weight %, about 1.5-4 weight %, 2.5-3.5 weight %, about 2.9 weight %, or about 2.94 weight %, based on the total weight of the formulation.

Provided compositions may be formulated into a unit dosage form. Such formulations are well known to one of ordinary skill in the art. In certain embodiments, the present invention provides a formulation comprising a solid dosage form as a tablet or capsule. In other embodiments, the present invention provides a solution for oral administration. In some embodiments, a unit dosage form contains about 1, 2, 3, 4, 5, 6, 7, 8, 9, 10, 20, 25, 40, 50 mg, 75 mg, 100 mg, 125 mg, 150 mg, 175 mg, 200 mg of Compound A. In some embodiments, a unit dosage form contains about from 1 to 100 mg, about 5-50 mg, or about 10-30 mg of Compound A. In some embodiments, a unit dosage form contains about 1, 2, 3, 4, 5, 6, 7, 8, 9, 10, 20, 25, 40, 50 mg. In some embodiments, a unit dosage form contains about 20 mg of Compound A.

In some embodiments, satisfactory results can be obtained when the compounds of the invention are administered at a daily dosage of from about 0.1 to about 500 mg/kg of body weight, optionally given in divided doses two to four times a day, or in sustained release form. The total daily dosage can be projected to be from about 1 to 1000 mg, preferably from about 0.1 to 100 mg. Dosage forms suitable for internal use comprise from about 0.1 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

For the treatment of cancer, the disclosed formulations of this invention can be administered in combination with other anti-tumor substances or with radiation therapy. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, anti-metabolites such as 5-fluorouracil or hydroxyurea, DNA intercalators such as adriamycin or bleomycin, topoisomerase inhibitors such as etoposide or camptothecin, antiangiogenic agents such as angiostatin, and antiestrogens such as tamoxifen.

Uses and Kits of the Compositions

Provided compositions, and formulations thereof, can also be useful in treatment of conditions including cancers.

In still further embodiments, veterinary applications (e.g., treatment of domestic animals, e.g. horse, dogs, cats, etc.) of use of disclosed compositions, and formulations thereof, are provided. Thus, use of provided formulations in veterinary applications analogous to those discussed above for human subjects is contemplated.

The disclosed compositions, and formulations thereof, can be employed in combination therapies, that is, a disclosed composition, or formulation thereof, can be administered concurrently with, prior to, or subsequent to, one or more other desired therapeutics or medical procedures. Particular combination therapies (therapeutics or procedures) to employ in a combination regimen can take into account compatibility of the desired therapeutics and/or procedures and the desired therapeutic effect to be achieved. Therapies thus employed may achieve a desired effect for the same disorder (for example, a formulation may be administered concurrently with another compound used to treat the same disorder), or they may achieve different effects (e.g., control of any adverse effects). As used herein, additional therapeutic compounds which are normally administered to treat or prevent a particular disease, or condition, are known as "appropriate for the disease, or condition, being treated".

In other embodiments, the disclosed compositions, and formulations thereof, and unit dose forms can be useful in preparation of medicaments, including, but not limited to medicaments useful in the treatment of cancer.

Still further encompassed by the invention are pharmaceutical packs and/or kits comprising disclosed compositions, and formulations thereof, and a container (e.g., a foil or plastic package, or other suitable container). Optionally instructions for use are additionally provided in such kits.

In order that the invention described herein may be more fully understood, the following examples are set forth. It should be understood that these examples are for illustrative purposes only and are not to be construed as limiting this invention in any manner.

EXAMPLES

Example 1. Preparation of (E)-N-(3-cyano-7-ethoxy-4-(3-ethynylphenylamino)quinolin-6-yl)-4-(dimethylamino)but-2-enamide (1)

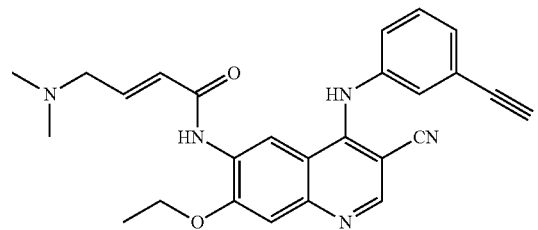 [SMILES: C#Cc1cccc(Nc2c(C#N)cnc3cc(OCC)c(NC(=O)/C=C/CN(C)C)cc23)c1]

A solution of (E)-4-(dimethylamino)but-2-enoic acid hydrochloride (1.28 g, 7.73 mmol) in THF (18 ml) and a catalytic amount of DMF was cooled to 5° C. while oxalyl chloride (0.67 ml, 7.0 mmol) was added slowly. The reaction mixture was then warmed to room temperature and stirred for 3 hours. A solution of 6-amino-7-ethoxy-4-(3-ethynylphenylamino)quinoline-3-carbonitrile (1.2 g, 3.66 mmol) in N-methyl-2-pyrolidinone (15 ml) was added dropwise over 10 minutes. The mixture was stirred overnight, quenched with water (200 ml). Aqueous sodium hydroxide solution was added to bring the pH to about 11. The mixture was further stirred for 1 hour, during which precipitates were formed. The resulting precipitates were collected by filtration and the collected solid was washed with water. The wet solid was then dried to give the title product 1 (1.43 g) as a free base compound. MS (ESI) m/z: 563 (M+1).

Example 2. Preparation of ((E)-N-[3-cyano-7-ethoxy-4-(3-ethynylanilino)-6-quinolyl]-4-(dimethylamino)but-2-enamide maleate (Compound A)

The free base compound 1 (1 eq.) is dissolved in a mixture of water and 1-propanol (1:9, v/v) and treated with maleic acid (1.03 eq.) at 40-50° C. for 1-2 hours. The mixture is cooled to room temperature and stayed overnight. Solids are collected by filtration to provide the title compound.

Example 3. Formulation Process

As shown in FIG. 1, Compound A and mannitol are mixed, thensifted through a 60 mesh sieve. Sodium starch glycolate is added and the resulting mixture is pre-mixed in an appropriate high-shear mixer or granulator at a stirring speed of about 7 revolution/second (r/s) and a shear speed of about 14 r/s for about 5 minutes. Hydroxypropyl cellulose aqueous solution (3%, w/w) is sprayed onto and mixed with the pre-mixed ingredients. The resulting mixture is granulated by amixture granulator at a stirring speed of about 7 r/s and a shear speed of about 14 r/s for about 4 to 8 minutes. Subsequently, the wet granulates are dried in a fluid bed dryer or a try dryer at about 60° C., and then sifted through a 20 mesh sieve. In parallel glyceryl behenate is sifted through a 60 mesh sieve. Then the sieved granules and the sieved glyceryl behenate areblended by a mixer at a stirring speed of about 15 revolution/minute for about 10 minutes, and subsequently filled into capsules.

Table 1 shows an example of the pharmaceutical composition filled in a capsule:

| Name | Function | Amount |
|---|---|---|
| Compound A | active agent | 20 mg |
| Mannitol | filler | 200 mg |
| Sodium Starch Glycolate | disintegrant | 10 mg |
| Hydroxypropyl Cellulose | binder | 1.1 mg |
| Glyceryl Behenate | lubricant | 7 mg |

Example 4. Compatibility Test of Excipients

Each of mannitol, sodium starch glycolate, hydroxypropyl cellulose and glyceryl behenate was individually mixed with Compound A. The resulting mixture was tested for the impurities over time under the following conditions: lumination 4500±500 Lux; high humidity at 90±5%; high temperature at 40±2° C.; and accelerated condition at humidity of 75±5% and temperature of 40±2° C. Testing were done at day 0, day 7 and day 14. The percentage of the total impurities and the SZMD4-Z8 impurity were recorded together with other data.

Table 2 shows selected results of the compatibility experiments:

| Name | Conditions | Days | SZMD4-Z8 | Total Impurities |
|---|---|---|---|---|
| API | | 0 | 0.03% | 0.29% |
| | lumination | 7 | 0.03% | 0.40% |
| | | 14 | 0.03% | 0.44%% |
| | humidity | 7 | 0.04% | 0.31% |
| | | 14 | 0.04% | 0.30% |
| | temperature | 7 | 0.03% | 0.31% |
| | | 14 | 0.03% | 0.30% |
| API + mannitol | | 0 | 0.04% | 0.30% |
| | lumination | 7 | 0.07% | 0.40% |
| | | 14 | 0.04% | 0.41% |
| | humidity | 7 | 0.04% | 0.33% |
| | | 14 | 0.05% | 0.31% |
| | temperature | 7 | 0.05% | 0.40% |
| | | 14 | 0.05% | 0.35% |
| API + Sodium starch glycolate | | 0 | 0.04% | 0.29% |
| | lumination | 7 | 0.04% | 0.35% |
| | | 14 | 0.05% | 0.47% |
| | humidity | 7 | 0.05% | 0.32% |
| | | 14 | 0.05% | 0.31% |
| | temperature | 7 | 0.04% | 0.31% |
| | | 14 | 0.05% | 0.32% |
| API + glyceryl behenate | | 0 | 0.05% | 0.43% |
| | lumination | 7 | 0.06% | 0.45% |
| | | 14 | 0.04% | 0.61% |
| | humidity | 7 | 0.07% | 0.39% |
| | | 14 | 0.03% | 0.39% |
| | temperature | 7 | 0.04% | 0.40% |
| | | 14 | 0.05% | 0.39% |
| API + mannitol, sodium starch glycolate, hydroxypropyl cellulose, glyceryl behenate | | 0 | 0.08% | 0.19% |
| | lumination | 7 | 0.10% | 0.34% |
| | | 14 | 0.08% | 0.38% |
| | humidity | 7 | 0.12% | 0.26% |
| | | 14 | 0.10% | 0.28% |
| | temperature | 7 | 0.13% | 0.25% |
| | | 14 | 0.09% | 0.23% |
| | accelerated | 7 | 0.09% | 0.22% |
| | | 14 | 0.12% | 0.29% |

Example 5. Stability Test of Fillers

Different fillers were used in formulations and the resulting formulations were tested for capsule accumulated dissolution and primary stability under accelerated conditions (humidity of 75±5% and temperature of 40±2° C.).

Table 3 shows the formulations 1-4 tested:

| Formulation No. | 1 | 2 | 3 | 4 |
|---|---|---|---|---|
| Compound A (mg) | 20 | 20 | 20 | 20 |
| Microcrystalline cellulose 102 (mg) | 200 | / | 150 | / |
| Mannitol (mg) | / | 200 | 50 | 200 |
| Crospovidone (mg) | 10 | 10 | / | / |
| Sodium starch glycolate (mg) | / | / | 10 | 10 |
| Hydroxypropyl cellulose (mg) | equiv. to 4.24 | equiv. to 1.02 | equiv. to 4.36 | equiv. to 1.09 |

-continued

| Formulation No. | 1 | 2 | 3 | 4 |
|---|---|---|---|---|
| Glyceryl behenate (mg) | 7 | 7 | 7 | 7 |
| Characteristics | off-white granules and powder | off-white granules and powder | off-white granules and powder | off-white granules and powder |
| Moisture (%) | 1.71 | 0.94 | 1.23 | 0.82 |

Note: as used herein the phrase "equiv. to" generally refers to "equivalent to".

Table 4 shows the results of the stability test under accelerated conditions:

|  | Formulation No. | SZMD4-Z8 | Total Impurities |
|---|---|---|---|
| 0 Days | 1 | 0.08% | 0.47% |
|  | 2 | 0.02% | 0.29% |
|  | 3 | 0.03% | 0.25% |
|  | 4 | 0.03% | 0.30% |
| 1 Month | 1 | 0.67% | 1.68% |
|  | 2 | 0.15% | 0.50% |
|  | 3 | 0.31% | 0.80% |
|  | 4 | 0.09% | 0.34% |
| 2 Months | 1 | 1.10% | 2.62% |
|  | 2 | 0.23% | 0.50% |
|  | 3 | 0.57% | 1.26% |
|  | 4 | 0.14% | 0.29% |

Example 6. Stability Test of Lubricants

Different lubricants were used in formulations and the resulting formulations were tested for disintegration and dissolution of the samples from a capsule.

Table 5 shows the formulations 5-11 tested and the results of disintegration:

Formulation Nos. 6, 8, 10, 11 and a control were further tested in an acetate buffer (pH about 4.0) for dissolution experiments. The control is the previous formulation.

Table 6 shows the results of the dissolution experiments showing the cumulative drug release:

| Formulation No. | | 6 | 8 | 10 | 11 | control |
|---|---|---|---|---|---|---|
| Cumulative drug release | 5 min | 21.37 | 46.59 | 65.53 | 71.77 | 62.96 |
|  | 10 min | 73.69 | 87.84 | 88.97 | 98.86 | 87.77 |
|  | 15 min | 92.84 | 96.70 | 90.02 | 99.66 | 91.81 |
|  | 30 min | 93.11 | 95.16 | 90.03 | 98.48 | 93.12 |
|  | 45 min | 94.80 | 97.49 | 90.10 | 100.46 | 93.86 |

Example 7. Types, Concentrations, and Amounts of the Binders

Different binders were used in formulations and the resulting formulations were tested for cumulative dissolution and preliminary stability of the samples from a capsule. For stability experiments, the formulations were tested under accelerated conditions (humidity of 75±5% and temperature of 40±2° C.).

Table 7 shows the formulations used when testing binders and the results of the accumulative dissolutionin an acetate buffer (pH about 4.0):

| Formulation No. | 5 | 6 | 7 | 8 | 9 | 10 | 11 |
|---|---|---|---|---|---|---|---|
| Compound A (mg) | 20 | 20 | 20 | 20 | 20 | 20 | 20 |
| Mannitol (mg) | 165 | 165 | 165 | 165 | 165 | 200 | 160 |
| Crospovidone (mg) | 9 | 9 | 9 | 9 | 9 | 10 | 9 |
| Povidon K30 (mg) | / | / | equiv. to 9.2 | / | / | equiv. to 6.27 | / |
| Hydroxypropyl cellulose (mg) | / | / | / | / | / | / | equiv. to 1.21 |
| Colloidal silica (mg) | 2 | 2 | 2 | 2 | 2 | 2 | 2 |
| Stearic acid (mg) | / | 2 | / | / | / | / | / |
| Magnesium stearate (mg) | 2 | / | 2 | / | / | / | / |
| Calcium stearate (mg) | / | / | / | / | 2 | / | / |
| Sodium stearyl fumarate (mg) | / | / | / | 2 | / | / | / |
| Glyceryl behenate (mg) | / | / | / | / | / | 4 | 4 |
| Intermediate | powder | powder | powder | powder | powder | granule | granule |
| Observation; time for total disintegration of the contents | Contents formed tubes; >15 min | Contents disintergrated; 6.2 min | Contents formed tubes; >10 min | Contents disintergrated; 5.2 min | Contents formed tubes; >15 min | / | Contents disintergrated; 7.2 min |

Note:
as used herein the phrase "equiv. to" generally refers to "equivalent to".

| Formulation No. | | 10 | 11 |
|---|---|---|---|
| Compound A (mg) | | 20 | 20 |
| Mannitol (mg) | | 160 | 200 |
| Crospovidone (mg) | | 10 | 0 |
| Hydroxypropyl cellulose (mg) | | / | 1.21 |
| Povidon K30 | | 6.27 | |
| Glyceryl behenate (mg) | | 4 | 4 |
| Colloidal silica (mg) | | 2 | 2 |
| Characteristics | | off-white granules and powder | off-white granules and powder |
| Moisture (%) | | 1.34 | 0.96 |
| Cumulative drug release | 5 min | 65.53 | 71.77 |
| | 10 min | 88.97 | 98.86 |
| | 15 min | 90.02 | 99.66 |
| | 30 min | 90.03 | 98.48 |
| | 45 min | 90.10 | 100.46 |

Table 8 shows the results of the stability test under accelerated conditions:

| | Formulation No. | SZMD4-Z8 | Total Impurities |
|---|---|---|---|
| 0 Days | 10 | 0.05% | 0.38% |
| | 11 | 0.12% | 0.30% |
| 14 days | 10 | 0.48% | 1.34% |
| | 11 | 0.09% | 0.25% |
| 1 Month | 10 | 0.77% | 1.47% |
| | 11 | 0.15% | 0.36% |

Further, different concentrations of hydroxypropyl cellulose solution were used in different formulations. The resulting formulations were tested for the flowability and accumulative dissolution.

Table 9 shows the formulations tested and the results of flowability and accumulative dissolution in an acetate buffer (pH about 4.0):

| Formulation No. | | 12 | 13 | 14 |
|---|---|---|---|---|
| Concentration of HPC aqueous solution (w/w) | | 3% | 5% | 7% |
| Compound A (mg) | | 20 | 20 | 20 |
| Mannitol (mg) | | 160 | 160 | 160 |
| Sodium starch glycolate (mg) | | 10 | 10 | 10 |
| Hydroxypropyl cellulose (mg) | | equiv. to 1.18 | equiv. to 1.80 | equiv. to 2.66 |
| Glyceryl behenate (mg) | | 4 | 4 | 4 |
| Characteristics | | off-white granules and powder | off-white granules and powder | off-white granules and powder |
| Angle of repose | | 45.8° | 45° | 45.8° |
| Moisture (%) | | 1.04 | 1.08 | 1.04 |
| Cumulative drug release | 5 min | 55.73 | 47.27 | 41.40 |
| | 10 min | 79.37 | 67.14 | 69.84 |
| | 15 min | 83.35 | 78.81 | 80.60 |
| | 30 min | 86.31 | 85.02 | 86.98 |
| | 45 min | 88.04 | 86.02 | 88.18 |

Note:
As used herein HPC refers to hydroxypropyl cellulose.
The phrase "equiv. to" refers to "equivalent to".

Example 8. Selection of Disintegrants

Different disintegrants were used in formulations and the resulting formulations were tested for cumulative dissolution and preliminary stability of the samples from a capsule. For stability experiments, the formulations were tested under accelerated conditions (humidity of 75±5% and temperature of 40±2° C.).

Table 10 shows the formulations used when testing disintegrants and the results of the accumulative dissolution in an acetate buffer (pH about 4.0):

| Formulation No. | 15 | 16 | 2 | 4 |
|---|---|---|---|---|
| Compound A (mg) | 20 | 20 | 20 | 20 |
| Mannitol (mg) | 160 | 160 | 200 | 200 |
| Crospovidone (mg) | 9 | / | 10 | / |
| Sodium starch glycolate (mg) | / | 10 | / | 10 |
| Hydroxypropyl cellulose (mg) | equiv. to 1.48 | equiv. to 1.10 | equiv. to 1.02 | equiv. to 1.09 |
| Glyceryl behenate (mg) | 4 | 4 | 7 | 7 |
| Theoretic load | 194.48 | 195.10 | 238.02 | 238.09 |
| Characteristics | off-white granules and powder | off-white granules and powder | off-white granules and powder | off-white granules and powder |

-continued

| Formulation No. | | 15 | 16 | 2 | 4 |
|---|---|---|---|---|---|
| Moisture (%) | | 1.11 | 0.97 | 0.94 | 0.82 |
| Cohesiveness in test runs | | cohesive | slightly cohesive | not cohesive | |
| Load differentials | | −15.92 to 14.18% | −13.21 to 12.33% | −6.07 to 5.30% | −4.61 to 2.56% |
| Cumulative drug release (%) | 5 min | 72.25 | 61.74 | 58.47 | 64.32 |
| | 10 min | 99.10 | 84.13 | 90.45 | 93.40 |
| | 15 min | 99.31 | 87.78 | 96.48 | 100.29 |
| | 30 min | 100.40 | 92.01 | 98.25 | 105.70 |
| | 45 min | 100.22 | 94.27 | 98.49 | 104.45 |

Table 11 shows the results of the stability test under accelerated conditions:

| | Formulation No. | SZMD4-Z8 | Total Impurities |
|---|---|---|---|
| 0 Days | 15 | 0.10% | 0.61% |
| | 16 | 0.15% | 0.23% |
| | 2 | 0.02% | 0.29% |
| | 4 | 0.03% | 0.30% |
| 1 Month | 15 | 0.22% | 0.65% |
| | 16 | 0.14% | 0.24% |
| | 2 | 0.15% | 0.50% |
| | 4 | 0.09% | 0.34% |
| 2 Months | 15 | 0.33% | 0.81% |
| | 16 | 0.20% | 0.37% |
| | 2 | 0.23% | 0.50% |
| | 4 | 0.14% | 0.29% |
| 3 Months | 15 | 0.43% | 1.00% |
| | 16 | 0.20% | 0.28% |
| | 2 | 0.38% | 0.75% |
| | 4 | 0.18% | 0.39% |

Example 9. Embodiments of the Formulation Process

A) Pretreatment of Ingredients

1) Weighing: each ingredient is measured according to the formulation;

2) Sieving: each of Compound A, mannitol and glyceryl behenate is sifted through 60 mesh sieve; and 3) Preparing the binder: dissolve the required amount of hydroxypropyl cellulose into water; adjust the volume of the solution to provide a final concentration of 3% (w/w).

B) Blending and Granulating

1) Placing the sifted Compound A and mannitol and sodium starch glycolate into a wet granulator; stirring and shearing for 5 min;

2) Adding the 3% (w/w) hydroxypropyl cellulose solution prepared in A) (about 2-4 minutes); stirring and shearing for another 2-4 minutes; and 3) The resulting wet product is squeezed into 20-mesh pellets using a micro pelletizer.

C) Drying and Milling

1) The wet pellets are dried at about 60±5° C. in a fluid bed dryer until the moisture content is less than 3%; and 2) Sifting: the dried pellets are sifted through a 20 mesh sieve.

D) Final Mixing

Placing the dried and sifted pellets into a mixer; add glyceryl behenate; mixing for 10 minutes; sampling the product to monitor the moisture (%) during the final mixing.

E) Bottling

Filling gelatin capsules with the mixed ingredients prepared above; controlling the weight differentials of the average load from about 92.5% to about 107.5%.

Example 10. Stability Test of Different Batches

Four batches of the new formulation (see, e.g., Table 1) were produced and compared with one batch of the previous formulation in stability tests under accelerated conditions (humidity of 75±5% and temperature of 40±2° C.).

Table 12 shows stability test results of the four batches (New 1-4) of the new formulation vs the previous formulation (Old) under accelerated conditions:

| | Batches | SZMD4-Z8 | Total Impurities |
|---|---|---|---|
| 0 Days | Old | 0.08 | 0.59 |
| | New 1 | 0.03 | 0.30 |
| | New 2 | 0.02 | 0.18 |
| | New 3 | 0.02 | 0.18 |
| | New 4 | 0.02 | 0.18 |
| 1 Month | Old | 0.26 | 0.56 |
| | New 1 | 0.09 | 0.34 |
| | New 2 | 0.09 | 0.25 |
| | New 3 | 0.10 | 0.25 |
| | New 4 | 0.09 | 0.24 |
| 2 Months | Old | 0.37 | 0.58 |
| | New 1 | 0.14 | 0.29 |
| | New 2 | 0.17 | 0.40 |
| | New 3 | 0.14 | 0.33 |
| | New 4 | 0.15 | 0.39 |
| 3 Months | Old | 0.52 | 1.11 |
| | New 1 | 0.18 | 0.38 |
| | New 2 | 0.18 | 0.49 |
| | New 3 | 0.18 | 0.58 |
| | New 4 | 0.17 | 0.49 |

Example 11. Further Stability Test of Different Batches Under Accelerated Conditions Three batches of the previous formulation (Old 1-3) and three batches of the new formulation (see, e.g., Table 1) were tested in stability tests under accelerated conditions (humidity of 75±5% and temperature of 40±2° C.)

Table 13 shows stability test results of the three batches (Old 1-3) of the previous formulation under accelerated conditions:

|  | Old 1 | | Old 2 | | Old 3 | |
| --- | --- | --- | --- | --- | --- | --- |
|  | SZMD4-Z8 | Total Impurities | SZMD4-Z8 | Total Impurities | SZMD4-Z8 | Total Impurities |
| 0 | 0.06% | 0.60% | 0.09% | 0.59% | 0.06% | 0.63% |
| 1 Month | 0.17% | 0.63% | 0.18% | 0.79% | 0.16% | 0.68% |
| 2 Months | 0.23% | 0.74% | 0.23% | 0.73% | 0.26% | 0.74% |
| 3 Months | 0.35% | 0.91% | 0.33% | 0.93% | 0.46% | 1.04% |
| 6 Months |  |  | Not applicable |  |  |  |

Table 14 shows stability test results of the three batches (New 4-6) of the new formulation under accelerated conditions:

|  | New 4 | | New 5 | | New 6 | |
| --- | --- | --- | --- | --- | --- | --- |
|  | SZMD4-Z8 | Total Impurities | SZMD4-Z8 | Total Impurities | SZMD4-Z8 | Total Impurities |
| 0 | 0.02% | 0.18% | 0.02% | 0.18% | 0.02% | 0.18% |
| 1 Month | 0.09% | 0.25% | 0.10% | 0.25% | 0.09% | 0.24% |
| 2 Months | 0.17% | 0.40% | 0.14% | 0.33% | 0.15% | 0.39% |
| 3 Months | 0.18% | 0.49% | 0.18% | 0.58% | 0.17% | 0.49% |
| 6 Months | 0.31% | 0.61% | 0.31% | 0.61% | 0.32% | 0.63% |

Example 12. Long-term Stability Test of Different Batches Under Normal Conditions Three batches of the new formulation (see, e.g., Table 1) and one batch of the previous formulation were tested in stability tests under normal conditions Table 15 shows stability test results of the one batch (Old 4) of the previous formulation and the three batches (New 4-6) of the new formulation under normal conditions

|  | Old 4 | | New 4 | | New 5 | | New 6 | |
| --- | --- | --- | --- | --- | --- | --- | --- | --- |
|  | SZMD4-Z8 | Total Imp. | SZMD4-Z8 | Total Imp. | SZMD4-Z8 | Total Imp. | SZMD4-Z8 | Total Imp. |
| 1 M | 0.09% | 0.45% | 0.02% | 0.18% | 0.02% | 0.18% | 0.02% | 0.18% |
| 3 M | 0.11% | 0.50% | 0.04% | 0.28% | 0.04% | 0.28% | 0.04% | 0.34% |
| 6 M | 0.18% | 0.54% | 0.03% | 0.28% | 0.07% | 0.30% | 0.09% | 0.32% |
| 9 M | 0.25% | 0.61% | / | / | / | / | / | / |
| 12 M | 0.40% | 0.74% | / | / | / | / | / | / |

Note:
As used herein the symbol "M" refers to "month(s)", the symbol "Imp." Refers to "Impurities".

What is claimed is:

1. A pharmaceutical formulation comprising:
   (i) about 20 mg of Compound A:

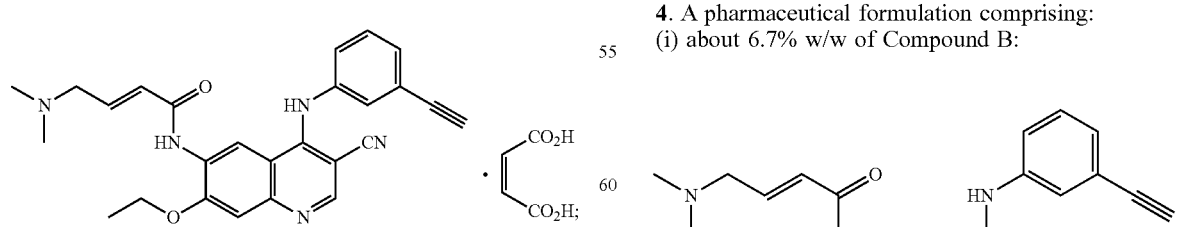

(ii) about 200 mg of mannitol;
   (iii) about 10 mg of sodium starch glycolate;
   (iv) about 1.1 mg of hydroxypropyl cellulose; and
   (v) about 7 mg of glyceryl behenate.

2. A capsule comprising the pharmaceutical formulation of claim 1.

3. A dry-filled capsule comprising the pharmaceutical formulation of claim 1.

4. A pharmaceutical formulation comprising:
   (i) about 6.7% w/w of Compound B:

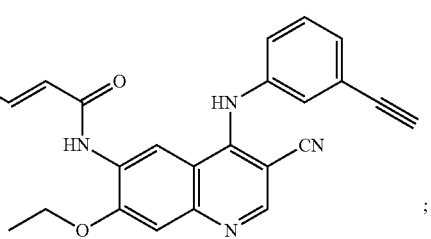

(ii) about 84% w/w mannitol;
(iii) about 4.2% w/w sodium starch glycolate;
(iv) about 0.46% w/w hydroxypropyl cellulose; and
(v) about 2.9% w/w glyceryl behenate.

5. A capsule comprising the pharmaceutical formulation of claim 4.

6. A dry-filled capsule comprising the pharmaceutical formulation of claim 4.

7. A pharmaceutical formulation comprising:
(i) about 16 mg of Compound B:

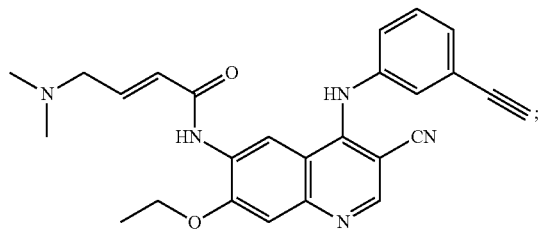 [SMILES: C#Cc1cccc(Nc2c(C#N)cnc3cc(OCC)c(NC(=O)/C=C/CN(C)C)cc23)c1]

(ii) about 200 mg of mannitol;
(iii) about 10 mg of sodium starch glycolate;
(iv) about 1.1 mg of hydroxypropyl cellulose; and
(v) about 7 mg of glyceryl behenate.

8. A capsule comprising the pharmaceutical formulation of claim 7.

9. A dry-filled capsule comprising the pharmaceutical formulation of claim 7.

10. A method for preparing a pharmaceutical formulation, comprising:
(a) sieving each of 5-10 weight percent of Compound A, 80-90 weight percent of one or more fillers, and 1.5-4 weight percent of one or more lubricants separately;
(b) dissolving 0.25-0.75 weight percent of one or more binders into water to make a solution having a concentration of 3 weight percent with respect to the one or more binders;
(c) stirring and shearing a mixture of the Compound A, the one or more fillers and 2-6% weight percent of one or more disintegrants;
(d) adding the solution of the one or more binders in (b) to the mixture in (c) to make a wet mixture;
(e) preparing wet pellets from the wet mixture in (d);
(f) drying the wet pellets in (e) to make dried pellets;
(g) sieving the dried pellets in (f) to make sifted pellets; and
(h) mixing the one or more lubricants to the sifted pellets in (g);
wherein Compound A is:

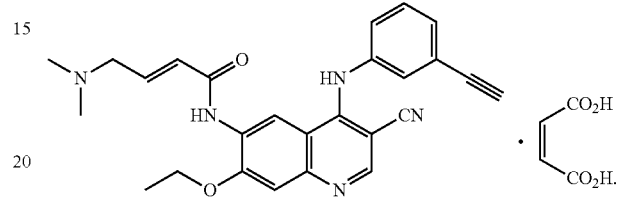

11. The method of claim 10, wherein the sieving in (a) is sifted through 60 mesh sieve.

12. The method of claim 11, wherein the wet pellets in (e) is about 20 mesh in size.

13. The method of claim 12, wherein the sieving in (g) is sifted through 20 mesh sieve.

14. The method of claim 13, wherein:
(i) the one or more fillers is mannitol;
(ii) the one or more disintegrants is sodium starch glycolate;
(iii) the one or more binders is hydroxypropyl cellulose; and
(iv) the one or more lubricants is glyceryl behenate.

15. A method for treating non-small cell lung cancer or breast cancer in a subject, comprising: administering an effective amount of a pharmaceutical formulation according to claim 7 to the subject.

* * * * *